US012599749B2

(12) United States Patent
Ullmann et al.

(10) Patent No.: US 12,599,749 B2
(45) Date of Patent: Apr. 14, 2026

(54) CONTROLLABLE INSERTION SLEEVE

(71) Applicant: KARDION GMBH, Stuttgart (DE)

(72) Inventors: Michael Ullmann, Leonberg (DE);
Hardy Baumbach, Stuttgart (DE); **Inga
Schellenberg**, Stuttgart (DE)

(73) Assignee: Kardion GmbH, Stuttgart (DE)

( * ) Notice: Subject to any disclaimer, the term of this
patent is extended or adjusted under 35
U.S.C. 154(b) by 1094 days.

(21) Appl. No.: 17/056,937

(22) PCT Filed: May 30, 2019

(86) PCT No.: PCT/EP2019/064129
§ 371 (c)(1),
(2) Date: Mar. 24, 2021

(87) PCT Pub. No.: WO2019/229206
PCT Pub. Date: Dec. 5, 2019

(65) Prior Publication Data
US 2021/0205585 A1 Jul. 8, 2021

(30) Foreign Application Priority Data

May 30, 2018 (DE) ..................... 10 2018 208 564.1

(51) Int. Cl.
*A61M 25/01* (2006.01)
*A61M 25/00* (2006.01)
*A61M 25/09* (2006.01)

(52) U.S. Cl.
CPC .... *A61M 25/0147* (2013.01); *A61M 25/0023*
(2013.01); *A61M 25/09* (2013.01);
(Continued)

(58) Field of Classification Search
CPC .......... A61M 25/0147; A61M 25/0023; A61M
25/09; A61M 2025/09175;
(Continued)

(56) References Cited

U.S. PATENT DOCUMENTS

| | | | |
|---|---|---|---|
| 3,568,659 | A | 3/1971 | Karnegis |
| 4,522,194 | A | 6/1985 | Normann |

(Continued)

FOREIGN PATENT DOCUMENTS

| | | |
|---|---|---|
| CA | 3 000 581 | 4/2017 |
| CN | 1524000 | 8/2004 |

(Continued)

OTHER PUBLICATIONS

International Preliminary Report on Patentability and Written Opinion received in PCT Application No. PCT/EP2019/064129, dated Dec. 10, 2020 in 8 pages.
(Continued)

*Primary Examiner* — James D Ponton
(74) *Attorney, Agent, or Firm* — Knobbe, Martens, Olson & Bear, LLP

(57) ABSTRACT
The present application relates to an insertion sleeve (2), in which a guide wire (3) extends in order to guide the insertion sleeve (2). A cavity (23) is formed in the sleeve wall (22), which cavity extends in parallel with a longitudinal direction of the insertion sleeve (2) over the whole length of the sleeve, wherein said cavity (23) accommodates the guide wire (3). In addition to the cavity (23) at least one control wire (4) is integrated into the sleeve wall (22), which at least one control wire is designed to cause a curvature of the insertion sleeve (2).

11 Claims, 4 Drawing Sheets

(52) U.S. Cl.
CPC ............... *A61M 2025/0037* (2013.01); *A61M 2025/09175* (2013.01)

(58) Field of Classification Search
CPC .......... A61M 25/0026; A61M 25/0021; A61M 25/0133; A61M 2025/015; A61M 2025/0037
See application file for complete search history.

(56) References Cited

U.S. PATENT DOCUMENTS

| | | | |
|---|---|---|---|
| 4,802,650 A | 2/1989 | Stricker | |
| 4,902,272 A | 2/1990 | Milder et al. | |
| 4,919,647 A | 4/1990 | Nash | |
| 4,921,479 A | 5/1990 | Grayzel | |
| 4,943,275 A | 7/1990 | Stricker | |
| 4,968,300 A | 11/1990 | Moutafis et al. | |
| 4,985,014 A | 1/1991 | Orejola | |
| 5,061,256 A | 10/1991 | Wampler | |
| 5,084,064 A | 1/1992 | Barak et al. | |
| 5,090,957 A | 2/1992 | Moutafis et al. | |
| 5,112,292 A | 5/1992 | Hwang et al. | |
| 5,116,305 A | 5/1992 | Milder et al. | |
| 5,322,509 A | 6/1994 | Rickerd | |
| 5,330,460 A | 7/1994 | Moss et al. | |
| 5,354,271 A | 10/1994 | Voda | |
| 5,409,463 A | 4/1995 | Thomas et al. | |
| 5,647,127 A | 7/1997 | Miyata et al. | |
| 5,752,937 A | 5/1998 | Otten et al. | |
| 5,921,913 A | 7/1999 | Siess | |
| 5,928,132 A | 7/1999 | Leschinsky | |
| 6,152,909 A * | 11/2000 | Bagaoisan .......... | A61M 25/104 604/173 |
| 6,159,198 A | 12/2000 | Gardeski et al. | |
| 6,176,848 B1 | 1/2001 | Rau et al. | |
| 6,450,948 B1 | 9/2002 | Matsuura et al. | |
| 6,497,681 B1 | 12/2002 | Brenner | |
| 6,530,876 B1 | 3/2003 | Spence | |
| 6,544,247 B1 | 4/2003 | Gardeski et al. | |
| 6,743,239 B1 | 6/2004 | Kuehn | |
| 6,794,789 B2 | 9/2004 | Siess et al. | |
| 6,879,126 B2 | 4/2005 | Paden et al. | |
| 7,022,100 B1 | 4/2006 | Aboul-Hosn et al. | |
| 7,166,088 B2 | 1/2007 | Heuser | |
| 7,241,257 B1 | 7/2007 | Ainsworth et al. | |
| 7,250,041 B2 | 7/2007 | Chiu et al. | |
| 7,357,794 B2 | 4/2008 | Makower et al. | |
| 7,419,486 B2 | 9/2008 | Kampa | |
| 7,621,894 B2 | 11/2009 | Leeflang et al. | |
| 7,722,568 B2 | 5/2010 | Lenker et al. | |
| 7,744,571 B2 | 6/2010 | Fisher et al. | |
| 7,824,375 B2 | 11/2010 | Hastings, Jr. et al. | |
| 7,841,976 B2 | 11/2010 | McBride et al. | |
| 7,878,967 B1 | 2/2011 | Khanal | |
| 7,951,119 B2 | 5/2011 | Leeflang et al. | |
| 8,012,079 B2 | 9/2011 | Delgado, III | |
| 8,025,647 B2 | 9/2011 | Siess et al. | |
| 8,043,263 B2 | 10/2011 | Helgeson et al. | |
| 8,088,154 B2 | 1/2012 | Hoffman et al. | |
| 8,152,845 B2 | 4/2012 | Bourque | |
| 8,157,719 B1 | 4/2012 | Ainsworth et al. | |
| 8,231,519 B2 | 7/2012 | Reichenbach et al. | |
| 8,262,619 B2 | 9/2012 | Chebator et al. | |
| 8,292,908 B2 | 10/2012 | Nieman et al. | |
| 8,343,028 B2 | 1/2013 | Gregoric et al. | |
| 8,382,830 B2 | 2/2013 | Maher et al. | |
| 8,475,431 B2 | 7/2013 | Howat | |
| 8,480,627 B2 | 7/2013 | Christiansen | |
| 8,485,961 B2 | 7/2013 | Campbell et al. | |
| 8,545,380 B2 | 10/2013 | Farnan et al. | |
| 8,579,966 B2 | 11/2013 | Seguin et al. | |
| 8,591,538 B2 | 11/2013 | Gellman | |
| 8,591,539 B2 | 11/2013 | Gellman | |
| 8,597,170 B2 | 12/2013 | Walters et al. | |
| 8,613,777 B2 | 12/2013 | Siess et al. | |
| 8,684,904 B2 | 4/2014 | Campbell et al. | |
| 8,721,517 B2 | 5/2014 | Zeng et al. | |
| 8,727,959 B2 | 5/2014 | Reitan et al. | |
| 8,728,055 B2 | 5/2014 | Stehr et al. | |
| 8,734,331 B2 | 5/2014 | Evans et al. | |
| 8,814,776 B2 | 8/2014 | Hastie et al. | |
| 8,852,173 B2 | 10/2014 | Sigg et al. | |
| 8,888,728 B2 | 11/2014 | Aboul-Hosn et al. | |
| 8,900,115 B2 | 12/2014 | Bolling et al. | |
| 8,926,564 B2 | 1/2015 | King et al. | |
| 8,932,246 B2 | 1/2015 | Ferrari | |
| 8,992,406 B2 | 3/2015 | Corbett | |
| 9,138,518 B2 | 9/2015 | Campbell et al. | |
| 9,144,669 B2 | 9/2015 | Wieselthaler | |
| 9,149,606 B2 | 10/2015 | Beissel et al. | |
| 9,162,017 B2 | 10/2015 | Evans et al. | |
| 9,168,060 B2 | 10/2015 | Voss | |
| 9,308,305 B2 | 4/2016 | Chen et al. | |
| 9,327,068 B2 | 5/2016 | Aboul-Hosn et al. | |
| 9,364,592 B2 | 6/2016 | McBride | |
| 9,402,942 B2 | 8/2016 | Hastie et al. | |
| 9,452,249 B2 | 9/2016 | Kearsley et al. | |
| 9,486,566 B2 | 11/2016 | Siess | |
| 9,510,813 B2 | 12/2016 | Levy et al. | |
| 9,539,094 B2 | 1/2017 | Dale et al. | |
| 9,539,378 B2 | 1/2017 | Tuseth | |
| 9,545,468 B2 | 1/2017 | Aboul-Hosn et al. | |
| 9,561,314 B2 | 2/2017 | Aboul-Hosn et al. | |
| 9,569,985 B2 | 2/2017 | Alkhatib et al. | |
| 9,585,991 B2 | 3/2017 | Spence | |
| 9,597,063 B2 | 3/2017 | Voss et al. | |
| 9,616,159 B2 | 4/2017 | Anderson et al. | |
| 9,656,011 B2 | 5/2017 | Graham et al. | |
| 9,669,144 B2 | 6/2017 | Spanier et al. | |
| 9,682,180 B2 | 6/2017 | Hoarau et al. | |
| 9,724,083 B2 | 8/2017 | Quadri et al. | |
| 9,744,279 B2 | 8/2017 | Tamez et al. | |
| 9,750,861 B2 | 9/2017 | Hastie et al. | |
| 9,769,912 B2 | 9/2017 | Helm et al. | |
| 9,782,905 B2 | 10/2017 | Drake et al. | |
| 9,789,238 B2 | 10/2017 | Aboul-Hosn et al. | |
| 9,807,860 B2 | 10/2017 | Helm et al. | |
| 9,814,813 B2 | 11/2017 | Corbett | |
| 9,814,814 B2 | 11/2017 | Corbett et al. | |
| 9,821,101 B2 | 11/2017 | Andrus et al. | |
| 9,821,146 B2 | 11/2017 | Tao et al. | |
| 9,827,356 B2 | 11/2017 | Muller et al. | |
| 9,872,948 B2 | 1/2018 | Siess | |
| 9,974,893 B2 | 5/2018 | Toellner | |
| 9,974,938 B2 | 5/2018 | Pepin et al. | |
| 9,999,714 B2 | 6/2018 | Spanier et al. | |
| 10,010,412 B2 | 7/2018 | Taft | |
| 10,080,871 B2 | 9/2018 | Schumacher et al. | |
| 10,123,875 B2 | 11/2018 | Wildhirt et al. | |
| 10,183,104 B2 | 1/2019 | Anderson et al. | |
| 10,207,037 B2 | 2/2019 | Corbett et al. | |
| 10,207,038 B2 | 2/2019 | Neumann | |
| 10,238,782 B2 | 3/2019 | Barry | |
| 10,238,783 B2 | 3/2019 | Aboul-Hosn et al. | |
| 10,258,771 B2 | 4/2019 | Beissel et al. | |
| 10,279,093 B2 | 5/2019 | Reichenbach et al. | |
| 10,300,185 B2 | 5/2019 | Aboul-Hosn et al. | |
| 10,300,249 B2 | 5/2019 | Tao et al. | |
| 10,350,384 B2 | 7/2019 | Farnan et al. | |
| 10,357,598 B2 | 7/2019 | Aboul-Hosn et al. | |
| 10,376,162 B2 | 8/2019 | Edelman et al. | |
| 10,441,771 B2 | 10/2019 | Bickhart et al. | |
| 10,449,279 B2 | 10/2019 | Muller | |
| 10,478,542 B2 | 11/2019 | Jahangir | |
| 10,493,191 B2 | 12/2019 | Whisenant et al. | |
| 10,537,431 B2 | 1/2020 | Zhou et al. | |
| 10,537,672 B2 | 1/2020 | Tuseth et al. | |
| 10,576,192 B2 | 3/2020 | Muller et al. | |
| 10,576,258 B2 | 3/2020 | Fantuzzi et al. | |
| 10,617,808 B2 | 4/2020 | Hastie et al. | |
| 10,709,828 B2 | 7/2020 | Toellner et al. | |
| 10,737,008 B2 | 8/2020 | Corbett et al. | |
| 10,737,086 B2 | 8/2020 | Agrawal et al. | |
| 10,806,904 B2 | 10/2020 | Jelle et al. | |

(56) References Cited

U.S. PATENT DOCUMENTS

| | | | |
|---|---|---|---|
| 10,857,274 B2 | 12/2020 | Alexander et al. |
| 10,864,015 B2 | 12/2020 | Von Segesser |
| 10,864,308 B2 | 12/2020 | Muller et al. |
| 10,881,836 B2 | 1/2021 | Schumacher et al. |
| 10,881,845 B2 | 1/2021 | Siess et al. |
| 10,894,143 B2 | 1/2021 | Yokoyama |
| 10,898,625 B2 | 1/2021 | Toellner |
| 10,953,205 B2 | 3/2021 | Korkuch |
| 10,959,878 B2 | 3/2021 | Wolfertz et al. |
| 10,967,152 B2 | 4/2021 | Korkuch |
| 11,007,350 B2 | 5/2021 | Tao et al. |
| 11,045,624 B2 | 6/2021 | Oiwa |
| 11,045,634 B2 | 6/2021 | Korkuch et al. |
| 11,058,851 B2 | 7/2021 | Farnan |
| 11,065,417 B2 | 7/2021 | Inukai et al. |
| 11,076,884 B2 | 8/2021 | Anderson et al. |
| 11,090,465 B2 | 8/2021 | Weber et al. |
| 11,096,568 B2 | 8/2021 | Harrah et al. |
| 11,129,959 B2 | 9/2021 | Hart et al. |
| 11,129,969 B2 | 9/2021 | Pederson, Jr. et al. |
| 11,173,295 B2 | 11/2021 | Mack et al. |
| 11,191,927 B2 | 12/2021 | McLaughlin et al. |
| 11,197,690 B2 | 12/2021 | Fantuzzi et al. |
| 11,219,755 B2 | 1/2022 | Siess et al. |
| 11,241,312 B2 | 2/2022 | Simonin |
| 11,266,502 B1 | 3/2022 | Wallace |
| 11,291,800 B2 | 4/2022 | Yokota |
| 11,291,805 B2 | 4/2022 | Ouchi et al. |
| 11,291,821 B2 | 4/2022 | Agrawal et al. |
| 11,291,855 B2 | 4/2022 | Wiesener |
| 11,304,747 B2 | 4/2022 | Simani et al. |
| 11,304,755 B2 | 4/2022 | Cao et al. |
| 11,311,311 B2 | 4/2022 | Sperry et al. |
| 11,318,284 B2 | 5/2022 | Ishida et al. |
| 11,318,285 B2 | 5/2022 | Ishida |
| 11,318,290 B2 | 5/2022 | Kleinhaus |
| 11,324,920 B2 | 5/2022 | Inukai et al. |
| 11,331,082 B2 | 5/2022 | Itoh et al. |
| 11,331,450 B2 | 5/2022 | Sakaguchi |
| 11,331,451 B2 | 5/2022 | Yamashita et al. |
| 11,351,359 B2 | 6/2022 | Clifton et al. |
| 11,364,363 B2 | 6/2022 | Fantuzzi et al. |
| 11,369,413 B2 | 6/2022 | Murphy |
| 11,377,512 B2 | 7/2022 | Kuramoto et al. |
| 11,389,633 B2 | 7/2022 | Rohl et al. |
| 11,400,261 B2 | 8/2022 | Mathews et al. |
| 11,406,395 B2 | 8/2022 | Wada et al. |
| 11,406,522 B2 | 8/2022 | Folan et al. |
| 11,406,798 B2 | 8/2022 | Kambara |
| 11,406,799 B2 | 8/2022 | McEvaddy et al. |
| 11,413,446 B2 | 8/2022 | Siess et al. |
| 11,419,721 B2 | 8/2022 | Poppe et al. |
| 11,419,743 B2 | 8/2022 | Poppe et al. |
| 11,426,562 B2 | 8/2022 | Fantuzzi |
| 11,439,791 B2 | 9/2022 | Ishida |
| 11,446,044 B2 | 9/2022 | Bonnette et al. |
| 11,446,414 B2 | 9/2022 | Oiwa |
| 11,452,575 B2 | 9/2022 | Morey et al. |
| 11,458,285 B2 | 10/2022 | Graham et al. |
| 11,471,026 B2 | 10/2022 | Piskun et al. |
| 11,471,663 B2 | 10/2022 | Tuval et al. |
| 11,471,665 B2 | 10/2022 | Clifton et al. |
| 11,484,698 B2 | 11/2022 | Radman |
| 11,497,889 B2 | 11/2022 | Mixter et al. |
| 11,497,894 B2 | 11/2022 | Korkuch et al. |
| 11,497,896 B2 | 11/2022 | Tanner et al. |
| 11,503,993 B2 | 11/2022 | Chu et al. |
| 11,504,102 B2 | 11/2022 | Stanton et al. |
| 11,511,083 B2 | 11/2022 | Wada |
| 11,511,084 B2 | 11/2022 | Chu |
| 11,511,098 B2 | 11/2022 | Agrawal et al. |
| 11,511,101 B2 | 11/2022 | Hastie et al. |
| 11,517,191 B2 | 12/2022 | Oskin |
| 11,517,720 B2 | 12/2022 | Korkuch et al. |
| 11,517,738 B2 | 12/2022 | Wisniewski |
| 11,523,905 B2 | 12/2022 | Griswold et al. |
| 11,524,137 B2 | 12/2022 | Jahangir |
| 11,524,153 B2 | 12/2022 | Alexander et al. |
| 11,529,510 B2 | 12/2022 | Leven |
| 11,540,857 B2 | 1/2023 | Olson et al. |
| 11,564,710 B2 | 1/2023 | Fitterer et al. |
| 11,565,093 B2 | 1/2023 | Kirt et al. |
| 11,583,670 B2 | 2/2023 | Pfeifer et al. |
| 11,602,448 B2 | 3/2023 | Nygaard et al. |
| 11,628,280 B2 | 4/2023 | Schumacher et al. |
| 11,633,574 B2 | 4/2023 | Watanabe |
| 11,642,511 B2 | 5/2023 | Delgado, III |
| 11,660,434 B2 | 5/2023 | Korkuch et al. |
| 11,679,250 B2 | 6/2023 | Alexander et al. |
| 11,690,606 B2 | 7/2023 | Muller et al. |
| 11,690,979 B2 | 7/2023 | Voss et al. |
| 11,690,997 B2 | 7/2023 | Georges et al. |
| 11,697,002 B2 | 7/2023 | Korkuch |
| 11,730,939 B2 | 8/2023 | Siess et al. |
| 11,730,942 B2 | 8/2023 | Fantuzzi et al. |
| D998,799 S | 9/2023 | Okamura et al. |
| 11,744,567 B2 | 9/2023 | Deuel et al. |
| 11,744,638 B2 | 9/2023 | Davies et al. |
| 11,751,751 B2 | 9/2023 | Calabrese et al. |
| 11,751,753 B2 | 9/2023 | Levasseur et al. |
| 11,752,308 B2 | 9/2023 | Tao et al. |
| 11,759,610 B2 | 9/2023 | Calabrese et al. |
| 11,766,264 B2 | 9/2023 | Phan et al. |
| 11,766,555 B2 | 9/2023 | Matthes et al. |
| 11,771,444 B2 | 10/2023 | Crawford et al. |
| 11,779,194 B2 | 10/2023 | Wilder et al. |
| 11,779,338 B2 | 10/2023 | Gordon et al. |
| 11,779,361 B2 | 10/2023 | Kugler et al. |
| 11,779,729 B2 | 10/2023 | Guimaraes et al. |
| 11,779,743 B2 | 10/2023 | Agrawal et al. |
| 11,786,109 B2 | 10/2023 | Golden et al. |
| 11,786,701 B2 | 10/2023 | Maki et al. |
| 11,786,720 B2 | 10/2023 | Muller |
| 11,793,530 B2 | 10/2023 | Chu et al. |
| 11,793,977 B2 | 10/2023 | Korkuch et al. |
| 11,806,046 B2 | 11/2023 | Fantuzzi et al. |
| 11,806,116 B2 | 11/2023 | Tuval et al. |
| 11,806,117 B2 | 11/2023 | Tuval et al. |
| 11,806,258 B2 | 11/2023 | Hingston et al. |
| 11,812,944 B2 | 11/2023 | Wales et al. |
| 11,812,951 B2 | 11/2023 | Mitelberg et al. |
| 11,812,952 B2 | 11/2023 | Abbott et al. |
| 11,813,183 B2 | 11/2023 | Christakis et al. |
| 11,813,445 B2 | 11/2023 | Alexander et al. |
| 11,826,517 B2 | 11/2023 | Fuller et al. |
| 11,832,793 B2 | 12/2023 | McWeeney et al. |
| 11,832,868 B2 | 12/2023 | Smail et al. |
| 11,833,314 B2 | 12/2023 | Corbett et al. |
| 11,833,316 B2 | 12/2023 | Hayakawa et al. |
| 11,833,342 B2 | 12/2023 | Tanner et al. |
| 11,844,592 B2 | 12/2023 | Tuval et al. |
| 11,844,909 B2 | 12/2023 | Tassoni et al. |
| 11,844,940 B2 | 12/2023 | D'Ambrosio et al. |
| 11,850,373 B2 | 12/2023 | Golden et al. |
| 11,857,159 B2 | 1/2024 | Saenz Villalobos et al. |
| 11,857,161 B2 | 1/2024 | Nguyen et al. |
| 11,857,197 B2 | 1/2024 | Alexander et al. |
| 11,857,740 B2 | 1/2024 | Chu |
| 11,857,743 B2 | 1/2024 | Fantuzzi et al. |
| 11,864,746 B2 | 1/2024 | Melilli et al. |
| 11,865,275 B2 | 1/2024 | O'Carrol et al. |
| 11,871,962 B2 | 1/2024 | Tehrani et al. |
| 11,877,753 B2 | 1/2024 | Connolly et al. |
| 11,878,131 B2 | 1/2024 | Pedersen et al. |
| 11,883,062 B2 | 1/2024 | Rawson |
| 11,883,274 B2 | 1/2024 | Schwammenthal et al. |
| D1,015,536 S | 2/2024 | Walsh |
| 11,890,085 B2 | 2/2024 | Duval et al. |
| 11,890,428 B2 | 2/2024 | Ito |
| 11,890,435 B2 | 2/2024 | Takagi |
| 11,896,474 B2 | 2/2024 | Hynes et al. |
| 11,896,482 B2 | 2/2024 | Delaloye et al. |
| 11,896,814 B2 | 2/2024 | Shambaugh, Jr. |
| 11,903,589 B2 | 2/2024 | Stahman et al. |

(56)　　　　　　References Cited

U.S. PATENT DOCUMENTS

| | | |
|---|---|---|
| 11,903,600 B2 | 2/2024 | Chu et al. |
| 11,903,831 B2 | 2/2024 | Shuey et al. |
| 11,903,857 B2 | 2/2024 | Folan |
| 11,911,072 B2 | 2/2024 | Fantuzzi et al. |
| 11,911,305 B2 | 2/2024 | Smith et al. |
| 11,918,186 B2 | 3/2024 | Chu et al. |
| 11,918,187 B2 | 3/2024 | Cahill et al. |
| 11,918,202 B2 | 3/2024 | Deuel et al. |
| 11,918,219 B2 | 3/2024 | Smith et al. |
| 11,918,470 B2 | 3/2024 | Jarral et al. |
| 11,918,752 B2 | 3/2024 | Tassoni et al. |
| 11,918,764 B2 | 3/2024 | Soltis et al. |
| 11,918,780 B2 | 3/2024 | Jagelski et al. |
| 11,925,315 B2 | 3/2024 | Chu et al. |
| 11,925,383 B2 | 3/2024 | Tada et al. |
| 11,925,386 B2 | 3/2024 | Favreau |
| 11,925,795 B2 | 3/2024 | Muller et al. |
| 11,930,996 B2 | 3/2024 | Dresher |
| 11,930,997 B2 | 3/2024 | Melito et al. |
| 11,931,003 B2 | 3/2024 | Congdon et al. |
| 11,931,058 B2 | 3/2024 | Spangler et al. |
| 11,931,068 B2 | 3/2024 | Fitterer et al. |
| 11,931,073 B2 | 3/2024 | Walsh et al. |
| 11,931,098 B2 | 3/2024 | Moriyama |
| 11,931,278 B2 | 3/2024 | Wood et al. |
| 11,931,528 B2 | 3/2024 | Rohl et al. |
| 11,931,530 B2 | 3/2024 | Campbell et al. |
| 11,937,774 B2 | 3/2024 | Wood et al. |
| 11,937,871 B2 | 3/2024 | Crawford et al. |
| 11,938,047 B2 | 3/2024 | Christakis et al. |
| 11,938,285 B2 | 3/2024 | Lau et al. |
| D1,028,246 S | 5/2024 | Delorenzo |
| 11,986,602 B2 | 5/2024 | Corbett |
| 11,986,604 B2 | 5/2024 | Siess |
| 12,017,076 B2 | 6/2024 | Tan et al. |
| 12,023,476 B2 | 7/2024 | Tuval et al. |
| 12,023,477 B2 | 7/2024 | Siess |
| 12,059,559 B2 | 8/2024 | Muller et al. |
| 12,064,614 B2 | 8/2024 | Agah et al. |
| 12,076,497 B2 | 9/2024 | Fantuzzi et al. |
| 12,121,681 B2 | 10/2024 | Korkuch |
| 12,138,438 B2 | 11/2024 | Alexander et al. |
| 12,161,855 B2 | 12/2024 | Hastie et al. |
| 12,161,857 B2 | 12/2024 | Saul et al. |
| 12,186,517 B2 | 1/2025 | Modlish et al. |
| 12,233,224 B2 | 2/2025 | Korkuch et al. |
| 12,239,799 B2 | 3/2025 | Corbett et al. |
| 12,263,330 B2 | 4/2025 | D'Ambrosio et al. |
| 12,268,860 B1 | 4/2025 | Fishman et al. |
| 12,290,673 B2 | 5/2025 | Jahangir |
| 12,296,134 B2 | 5/2025 | Siess et al. |
| 12,318,560 B2 | 6/2025 | O'Carrol et al. |
| 12,337,163 B2 | 6/2025 | Radman |
| 12,343,516 B2 | 7/2025 | Cook |
| 12,357,801 B2 | 7/2025 | Korkuch et al. |
| 12,369,944 B2 | 7/2025 | Fantuzzi et al. |
| 12,370,357 B2 | 7/2025 | Corbett et al. |
| D1,090,825 S | 8/2025 | Loughlin et al. |
| D1,090,829 S | 8/2025 | Loughlin et al. |
| 12,397,146 B2 | 8/2025 | Hart et al. |
| 12,402,910 B2 | 9/2025 | Korkuch |
| 12,403,287 B2 | 9/2025 | Tao et al. |
| 12,403,296 B2 | 9/2025 | Baumbach et al. |
| 12,409,299 B2 | 9/2025 | Fantuzzi et al. |
| 12,440,663 B2 | 10/2025 | Tuval et al. |
| 12,447,309 B2 | 10/2025 | Siess et al. |
| 12,447,316 B2 | 10/2025 | Voss et al. |
| 12,453,848 B2 | 10/2025 | Tuval et al. |
| 12,458,792 B2 | 11/2025 | Zarins |
| 12,478,774 B2 | 11/2025 | Muller |
| 12,478,775 B2 | 11/2025 | Schlebusch et al. |
| 12,485,261 B2 | 12/2025 | Siess et al. |
| 2002/0052638 A1* | 5/2002 | Zadno-Azizi .... A61B 17/12109 623/1.2 |
| 2002/0077600 A1 | 6/2002 | Sirimanne |
| 2002/0107482 A1 | 8/2002 | Rocamora et al. |
| 2003/0032941 A1 | 2/2003 | Boyle et al. |
| 2004/0034411 A1 | 2/2004 | Quijano |
| 2004/0044266 A1 | 3/2004 | Siess et al. |
| 2004/0102674 A1 | 5/2004 | Zadini et al. |
| 2005/0182435 A1 | 8/2005 | Andrews et al. |
| 2005/0272975 A1* | 12/2005 | McWeeney ........... A61B 1/307 600/172 |
| 2006/0155158 A1 | 7/2006 | Aboul-Hosn |
| 2006/0224110 A1 | 10/2006 | Scott et al. |
| 2008/0086027 A1 | 4/2008 | Siess et al. |
| 2008/0097293 A1 | 4/2008 | Chin et al. |
| 2008/0097386 A1 | 4/2008 | Osypka |
| 2008/0114339 A1 | 5/2008 | McBride et al. |
| 2008/0183136 A1 | 7/2008 | Lenker et al. |
| 2008/0269822 A1 | 10/2008 | Ljungstrom et al. |
| 2009/0054840 A1 | 2/2009 | Drake et al. |
| 2009/0069886 A1 | 3/2009 | Suri et al. |
| 2009/0182200 A1* | 7/2009 | Golden ............. A61M 25/0043 600/153 |
| 2009/0203957 A1 | 8/2009 | LaRose et al. |
| 2011/0034874 A1 | 2/2011 | Reitan |
| 2011/0124962 A1 | 5/2011 | Gordin |
| 2011/0230821 A1 | 9/2011 | Babic |
| 2011/0282274 A1 | 11/2011 | Fulton, III |
| 2012/0029265 A1 | 2/2012 | LaRose |
| 2012/0035645 A1 | 2/2012 | Gross |
| 2012/0221021 A1 | 8/2012 | Hoarau et al. |
| 2012/0296313 A1 | 11/2012 | Andreacchi et al. |
| 2013/0085318 A1 | 4/2013 | Toellner |
| 2013/0211324 A1 | 8/2013 | Voss et al. |
| 2013/0303831 A1 | 11/2013 | Evans |
| 2013/0303970 A1 | 11/2013 | Keenan et al. |
| 2014/0005467 A1 | 1/2014 | Farnan et al. |
| 2014/0180250 A1 | 6/2014 | Belson |
| 2015/0045696 A1* | 2/2015 | Osypka ............. A61M 25/0147 600/585 |
| 2015/0066082 A1 | 3/2015 | Moshe |
| 2015/0090372 A1 | 4/2015 | Branagan et al. |
| 2015/0119633 A1 | 4/2015 | Haselby et al. |
| 2015/0141738 A1 | 5/2015 | Toellner et al. |
| 2015/0151087 A1 | 6/2015 | Suzuki et al. |
| 2015/0290372 A1 | 10/2015 | Muller et al. |
| 2015/0290432 A1 | 10/2015 | Mathews et al. |
| 2015/0306291 A1 | 10/2015 | Bonde et al. |
| 2015/0343179 A1 | 12/2015 | Schumacher et al. |
| 2015/0359952 A1 | 12/2015 | Andrus et al. |
| 2016/0095744 A1 | 4/2016 | Wolfertz et al. |
| 2016/0256620 A1 | 9/2016 | Scheckel et al. |
| 2016/0271309 A1 | 9/2016 | Throckmorton et al. |
| 2017/0043074 A1 | 2/2017 | Siess |
| 2017/0065267 A1 | 3/2017 | Fantuzzi et al. |
| 2017/0080199 A1 | 3/2017 | Murphy |
| 2017/0143938 A1 | 5/2017 | Ogle et al. |
| 2017/0209099 A1* | 7/2017 | Caron ................ A61B 5/02154 |
| 2017/0215918 A1 | 8/2017 | Tao et al. |
| 2017/0232169 A1 | 8/2017 | Muller |
| 2017/0232170 A1 | 8/2017 | Jarvik |
| 2017/0232171 A1 | 8/2017 | Roehn et al. |
| 2017/0312492 A1 | 11/2017 | Fantuzzi et al. |
| 2017/0368245 A1 | 12/2017 | Kantrowitz et al. |
| 2018/0001003 A1 | 1/2018 | Moran et al. |
| 2018/0015214 A1 | 1/2018 | Lynch |
| 2018/0093070 A1 | 4/2018 | Cottone |
| 2018/0099076 A1 | 4/2018 | LaRose |
| 2018/0099078 A1 | 4/2018 | Tuseth et al. |
| 2018/0104397 A1 | 4/2018 | Schumacher |
| 2018/0200422 A1 | 7/2018 | Nguyen et al. |
| 2018/0207334 A1 | 7/2018 | Siess |
| 2018/0243004 A1 | 8/2018 | von Segesser et al. |
| 2018/0296742 A1 | 10/2018 | Toellner |
| 2018/0303990 A1 | 10/2018 | Siess et al. |
| 2018/0318547 A1 | 11/2018 | Yokoyama |
| 2018/0326131 A1 | 11/2018 | Muller et al. |
| 2018/0344987 A1 | 12/2018 | Lancette et al. |
| 2019/0001103 A1 | 1/2019 | Korkuch |
| 2019/0015232 A1 | 1/2019 | Tuseth et al. |
| 2019/0015568 A1 | 1/2019 | Tuseth |
| 2019/0015570 A1 | 1/2019 | Muller |

(56) References Cited

U.S. PATENT DOCUMENTS

| | | | |
|---|---|---|---|
| 2019/0060543 A1 | 2/2019 | Khanal et al. | |
| 2019/0069898 A1 | 3/2019 | Farnan | |
| 2019/0076167 A1 | 3/2019 | Fantuzzi et al. | |
| 2019/0083082 A1 | 3/2019 | Tassoni, Jr. et al. | |
| 2019/0083690 A1 | 3/2019 | Siess et al. | |
| 2019/0167122 A1 | 6/2019 | Obermiller et al. | |
| 2019/0167305 A1 | 6/2019 | Pedersen et al. | |
| 2019/0184078 A1 | 6/2019 | Zilbershlag et al. | |
| 2019/0223877 A1 | 7/2019 | Nitzen et al. | |
| 2019/0224390 A1 | 7/2019 | Barry | |
| 2019/0231523 A1 | 8/2019 | Lombardi | |
| 2019/0232025 A1 | 8/2019 | Tao et al. | |
| 2019/0247627 A1 | 8/2019 | Korkuch et al. | |
| 2019/0282741 A1 | 9/2019 | Franano et al. | |
| 2019/0290817 A1 | 9/2019 | Guo et al. | |
| 2019/0298974 A1 | 10/2019 | Siess et al. | |
| 2019/0321527 A1 | 10/2019 | King et al. | |
| 2019/0344000 A1 | 11/2019 | Kushwaha et al. | |
| 2019/0344052 A1 | 11/2019 | Klepetko | |
| 2019/0365975 A1 | 12/2019 | Muller et al. | |
| 2019/0381226 A1 | 12/2019 | Morozov et al. | |
| 2020/0000988 A1 | 1/2020 | Epple | |
| 2020/0000989 A1 | 1/2020 | Matheis et al. | |
| 2020/0022811 A1 | 1/2020 | Griswold | |
| 2020/0023109 A1 | 1/2020 | Epple | |
| 2020/0023110 A1 | 1/2020 | Jahangir | |
| 2020/0023113 A1 | 1/2020 | Epple et al. | |
| 2020/0054857 A1 | 2/2020 | Scheckel | |
| 2020/0054861 A1 | 2/2020 | Korkuch et al. | |
| 2020/0086021 A1 | 3/2020 | Jeevanandam et al. | |
| 2020/0094019 A1 | 3/2020 | Siess et al. | |
| 2020/0121905 A1 | 4/2020 | Zoll | |
| 2020/0129684 A1 | 4/2020 | Pfeffer et al. | |
| 2020/0139028 A1 | 5/2020 | Scheckel et al. | |
| 2020/0147283 A1 | 5/2020 | Tanner et al. | |
| 2020/0155739 A1 | 5/2020 | Siess et al. | |
| 2020/0164125 A1 | 5/2020 | Muller et al. | |
| 2020/0179657 A1 | 6/2020 | Liu | |
| 2020/0261633 A1 | 8/2020 | Spanier | |
| 2020/0345337 A1 | 11/2020 | Muller et al. | |
| 2021/0093836 A1 | 4/2021 | Fantuzzi | |
| 2021/0146116 A1 | 5/2021 | Siess | |
| 2021/0275791 A1 | 9/2021 | Korkuch et al. | |
| 2021/0290931 A1 | 9/2021 | Baumbach | |
| 2021/0290939 A1 | 9/2021 | Baumbach | |
| 2021/0379352 A1 | 12/2021 | Schlebusch et al. | |
| 2022/0008053 A1 | 1/2022 | Fitzgerald et al. | |
| 2022/0096125 A1 | 3/2022 | Fantuzzi et al. | |
| 2022/0161018 A1 | 5/2022 | Mitze et al. | |
| 2022/0161019 A1 | 5/2022 | Mitze et al. | |
| 2022/0161021 A1 | 5/2022 | Mitze et al. | |
| 2022/0339400 A1 | 10/2022 | Fantuzzi et al. | |
| 2023/0091199 A1 | 3/2023 | Siess et al. | |
| 2023/0145482 A1 | 5/2023 | Garrigue | |
| 2023/0233834 A1 | 7/2023 | Alexander et al. | |
| 2023/0277833 A1 | 9/2023 | Sharma et al. | |
| 2023/0293878 A1 | 9/2023 | Christof et al. | |
| 2023/0398330 A1 | 12/2023 | Mitze et al. | |
| 2023/0405286 A1 | 12/2023 | Schumacher et al. | |
| 2024/0074828 A1 | 3/2024 | Wenning | |
| 2024/0165392 A1 | 5/2024 | Liu et al. | |
| 2024/0269451 A1 | 8/2024 | Siess et al. | |
| 2025/0082922 A1 | 3/2025 | Fabiunke et al. | |
| 2025/0134652 A1 | 5/2025 | Maiorano | |

FOREIGN PATENT DOCUMENTS

| | | |
|---|---|---|
| CN | 102438552 | 5/2012 |
| CN | 204106671 | 1/2015 |
| CN | 106512117 | 3/2017 |
| CN | 107080871 | 8/2017 |
| CN | 206443963 | 8/2017 |
| CN | 107206139 | 9/2017 |
| CN | 107412892 | 12/2017 |
| CN | 207708250 | 8/2018 |
| CN | 106902404 | 8/2019 |
| CN | 110237327 | 9/2019 |
| CN | 209790495 | 12/2019 |
| CN | 110665079 | 1/2020 |
| CN | 112168427 | 1/2021 |
| CN | 113413544 | 9/2021 |
| CN | 215691046 | 2/2022 |
| CN | 114886614 | 8/2022 |
| CN | 115916111 | 4/2023 |
| CN | 218922664 | 4/2023 |
| CN | 116271502 | 6/2023 |
| CN | 116688321 | 10/2023 |
| CN | 117959584 | 5/2024 |
| CN | 118717356 | 10/2024 |
| CN | 119033506 | 11/2024 |
| DE | 10 2009 011 726 | 9/2010 |
| DE | 10 2009 047 845 | 3/2011 |
| DE | 11 2009 000 185 | 3/2013 |
| DE | 20 2013 007 408 | 12/2014 |
| DE | 10 2014 212 323 | 12/2015 |
| DE | 10 2016 122 268 | 5/2018 |
| DE | 10 2018 208 537 | 12/2019 |
| DE | 10 2018 208 564 | 12/2019 |
| DE | 10 2018 211 297 | 1/2020 |
| EP | 0 064 212 | 11/1982 |
| EP | 0 411 605 | 2/1991 |
| EP | 0 629 412 | 12/1994 |
| EP | 0 898 481 | 1/2002 |
| EP | 1 105 181 | 2/2004 |
| EP | 1 660 164 | 4/2009 |
| EP | 2 039 390 | 11/2010 |
| EP | 2 436 417 | 4/2012 |
| EP | 2 716 242 | 4/2014 |
| EP | 2 015 821 | 5/2015 |
| EP | 2 519 273 | 8/2015 |
| EP | 2 680 896 | 1/2016 |
| EP | 2 475 415 | 6/2016 |
| EP | 2 934 649 | 11/2016 |
| EP | 2 646 068 | 3/2017 |
| EP | 3 398 625 | 11/2018 |
| EP | 3 131 599 | 2/2019 |
| EP | 3 508 245 | 7/2019 |
| EP | 3 187 222 | 9/2019 |
| EP | 3 077 038 | 10/2019 |
| EP | 2 962 720 | 1/2020 |
| EP | 1 819 391 | 2/2020 |
| EP | 3 189 862 | 2/2020 |
| EP | 3 618 886 | 3/2020 |
| EP | 2 922 593 | 4/2020 |
| EP | 3 180 064 | 4/2020 |
| EP | 3 131 597 | 12/2020 |
| EP | 3 419 711 | 3/2021 |
| EP | 4 271 461 | 3/2021 |
| EP | 3 131 615 | 6/2021 |
| EP | 3 323 465 | 7/2021 |
| EP | 3 570 926 | 7/2021 |
| EP | 3 851 151 | 7/2021 |
| EP | 3 247 440 | 8/2021 |
| EP | 3 656 293 | 8/2021 |
| EP | 3 006 072 | 9/2021 |
| EP | 3 351 209 | 10/2021 |
| EP | 3 592 411 | 11/2021 |
| EP | 3 618 884 | 11/2021 |
| EP | 3 914 330 | 12/2021 |
| EP | 3 337 530 | 3/2022 |
| EP | 2 967 630 | 4/2022 |
| EP | 3 755 237 | 4/2022 |
| EP | 3 978 060 | 4/2022 |
| EP | 3 153 205 | 5/2022 |
| EP | 3 407 811 | 5/2022 |
| EP | 3 124 071 | 6/2022 |
| EP | 3 636 312 | 6/2022 |
| EP | 3 661 436 | 6/2022 |
| EP | 3 231 395 | 8/2022 |
| EP | 4 039 320 | 8/2022 |
| EP | 3 487 550 | 9/2022 |
| EP | 3 756 721 | 9/2022 |
| EP | 3 834 876 | 9/2022 |
| EP | 3 849 646 | 10/2022 |

(56)  References Cited

FOREIGN PATENT DOCUMENTS

| | | |
|---|---|---|
| EP | 3 000 493 | 11/2022 |
| EP | 3 028 736 | 11/2022 |
| EP | 3 077 035 | 11/2022 |
| EP | 3 305 357 | 11/2022 |
| EP | 3 389 530 | 11/2022 |
| EP | 3 570 762 | 11/2022 |
| EP | 3 579 905 | 11/2022 |
| EP | 3 858 422 | 11/2022 |
| EP | 3 866 876 | 11/2022 |
| EP | 3 199 198 | 12/2022 |
| EP | 3 270 999 | 12/2022 |
| EP | 3 398 562 | 12/2022 |
| EP | 3 402 562 | 12/2022 |
| EP | 3 538 173 | 3/2023 |
| EP | 3 551 271 | 7/2023 |
| EP | 3 692 933 | 9/2023 |
| EP | 3 713 634 | 9/2023 |
| EP | 3 773 130 | 9/2023 |
| EP | 3 895 638 | 9/2023 |
| EP | 3 903 701 | 9/2023 |
| EP | 3 178 515 | 10/2023 |
| EP | 3 253 302 | 10/2023 |
| EP | 3 603 727 | 10/2023 |
| EP | 3 773 129 | 10/2023 |
| EP | 3 777 952 | 10/2023 |
| EP | 4 052 754 | 10/2023 |
| EP | 4 149 606 | 10/2023 |
| EP | 3 515 525 | 11/2023 |
| EP | 3 583 927 | 11/2023 |
| EP | 3 744 362 | 11/2023 |
| EP | 3 766 428 | 11/2023 |
| EP | 3 773 363 | 11/2023 |
| EP | 3 840 670 | 11/2023 |
| EP | 3 711 698 | 12/2023 |
| EP | 3 752 236 | 12/2023 |
| EP | 3 349 671 | 1/2024 |
| EP | 3 349 839 | 1/2024 |
| EP | 3 443 915 | 1/2024 |
| EP | 3 487 421 | 1/2024 |
| EP | 3 784 305 | 1/2024 |
| EP | 3 925 659 | 1/2024 |
| EP | 3 242 613 | 2/2024 |
| EP | 3 509 504 | 2/2024 |
| EP | 3 518 836 | 2/2024 |
| EP | 3 534 805 | 2/2024 |
| EP | 3 566 636 | 2/2024 |
| EP | 3 603 728 | 2/2024 |
| EP | 3 700 464 | 2/2024 |
| EP | 3 718 588 | 2/2024 |
| EP | 3 768 342 | 2/2024 |
| EP | 3 820 412 | 2/2024 |
| EP | 3 053 532 | 3/2024 |
| EP | 3 142 573 | 3/2024 |
| EP | 3 275 499 | 3/2024 |
| EP | 3 397 147 | 3/2024 |
| EP | 3 424 551 | 3/2024 |
| EP | 3 492 042 | 3/2024 |
| EP | 3 528 885 | 3/2024 |
| EP | 3 563 805 | 3/2024 |
| EP | 3 927 254 | 3/2024 |
| EP | 3 955 796 | 3/2024 |
| EP | 4 037 574 | 3/2024 |
| EP | 4 140 532 | 5/2024 |
| EP | 3 970 765 | 7/2024 |
| EP | 3 789 054 | 8/2024 |
| EP | 3 793 633 | 8/2024 |
| EP | 4 419 042 | 8/2024 |
| EP | 4 429 750 | 9/2024 |
| EP | 3 534 985 | 10/2024 |
| EP | 3 893 957 | 10/2024 |
| EP | 3 641 845 | 11/2024 |
| EP | 3 643 350 | 11/2024 |
| EP | 4 034 221 | 11/2024 |
| EP | 3 522 947 | 2/2025 |
| EP | 4 429 754 | 2/2025 |
| EP | 4 429 751 | 3/2025 |
| EP | 4 429 752 | 3/2025 |
| EP | 4 429 753 | 3/2025 |
| EP | 3 958 921 | 5/2025 |
| EP | 3 463 539 | 6/2025 |
| EP | 4 100 091 | 7/2025 |
| EP | 3 908 177 | 8/2025 |
| EP | 3 706 853 | 10/2025 |
| EP | 4 046 678 | 10/2025 |
| GB | 2 451 161 | 12/2011 |
| GB | 2 545 750 | 6/2017 |
| JP | S59-076463 | 5/1984 |
| JP | H04-176471 | 6/1992 |
| JP | H08-504621 | 5/1996 |
| JP | H09-028664 | 2/1997 |
| JP | 2001-515374 | 9/2001 |
| JP | 6267625 | 1/2018 |
| WO | WO 97/037697 | 10/1997 |
| WO | WO 2005/007024 | 1/2005 |
| WO | WO 2005/028014 | 3/2005 |
| WO | WO 2007/006055 | 1/2007 |
| WO | WO 2007/044510 | 4/2007 |
| WO | WO 2008/106103 | 9/2008 |
| WO | WO 2009/114456 | 9/2009 |
| WO | WO 2010/014418 | 2/2010 |
| WO | WO 2010/092347 | 8/2010 |
| WO | WO 2011/096975 | 8/2011 |
| WO | WO 2011/160858 | 12/2011 |
| WO | WO 2013/013248 | 1/2013 |
| WO | WO 2013/092971 | 6/2013 |
| WO | WO 2013/093058 | 6/2013 |
| WO | WO 2014/096408 | 6/2014 |
| WO | WO 2015/019132 | 2/2015 |
| WO | WO 2015/134944 | 9/2015 |
| WO | WO 2016/028644 | 2/2016 |
| WO | WO 2016/055368 | 4/2016 |
| WO | WO 2017/053361 | 3/2017 |
| WO | WO 2017/053988 | 3/2017 |
| WO | WO 2017/060257 | 4/2017 |
| WO | WO 2017/118738 | 7/2017 |
| WO | WO 2017/147103 | 8/2017 |
| WO | WO 2017/157884 | 9/2017 |
| WO | WO 2017/194562 | 11/2017 |
| WO | WO 2018/078615 | 5/2018 |
| WO | WO 2018/081040 | 5/2018 |
| WO | WO 2018/165519 | 9/2018 |
| WO | WO 2018/202779 | 11/2018 |
| WO | WO 2018/234454 | 12/2018 |
| WO | WO 2019/035804 | 2/2019 |
| WO | WO 2019/038343 | 2/2019 |
| WO | WO 2019/038345 | 2/2019 |
| WO | WO 2019/055591 | 3/2019 |
| WO | WO 2019/067233 | 4/2019 |
| WO | WO 2019/118371 | 6/2019 |
| WO | WO 2019/161245 | 8/2019 |
| WO | WO 2019/180181 | 9/2019 |
| WO | WO 2019/191245 | 10/2019 |
| WO | WO 2019/193604 | 10/2019 |
| WO | WO 2019/219883 | 11/2019 |
| WO | WO 2019/229206 | 12/2019 |
| WO | WO 2019/229207 | 12/2019 |
| WO | WO 2019/229223 | 12/2019 |
| WO | WO 2019/229224 | 12/2019 |
| WO | WO 2020/003110 | 1/2020 |
| WO | WO 2020/011760 | 1/2020 |
| WO | WO 2020/123333 | 6/2020 |
| WO | WO 2020/132211 | 6/2020 |
| WO | WO 2020/137708 | 7/2020 |
| WO | WO 2020/219430 | 10/2020 |
| WO | WO 2021/062265 | 4/2021 |
| WO | WO 2021/150777 | 7/2021 |
| WO | WO 2023/040546 | 12/2021 |
| WO | WO 2022/011095 | 1/2022 |
| WO | WO 2022/032286 | 2/2022 |
| WO | WO 2022/091784 | 5/2022 |
| WO | WO 2022/109589 | 5/2022 |
| WO | WO 2022/109591 | 5/2022 |
| WO | WO 2023/003937 | 1/2023 |
| WO | WO 2024/125157 | 5/2023 |

(56) References Cited

FOREIGN PATENT DOCUMENTS

| | | |
|---|---|---|
| WO | WO 2023/112044 | 6/2023 |
| WO | WO 2023/230157 | 11/2023 |
| WO | WO 2024/243154 | 11/2024 |
| WO | WO 2025/075927 | 4/2025 |

OTHER PUBLICATIONS

International Search Report and Written Opinion received in PCT Application No. PCT/EP2019/064129, dated Aug. 23, 2019 in 11 pages.

Park et al., "A Novel Electrical Potential Sensing Method for in Vitro Stent Fracture Monitoring and Detection", Jan. 1, 2011, vol. 21, No. 4, pp. 213-222.

"Edwards Sapien 3 Kit—Transapical and Transaortic", Edwards Lifesciences, Released Nov. 8, 2016, p. 11. Chrome- extension:// efaidnbmnnnibpcajpcglclefindmkaj/https://edwardsprod.blob.core. windows.net/media/De/sapien3/doc-0045537b%20-%20certitude. pdf.

Gopinath, Divya, "A System for Impedance Characterization of Coronary Stents", University of Strathclyde Engineering, Thesis, Aug. 2015, p. 77.

"Transvalvular Insertion Tool (TVI)", Pressure Products, Feb. 2013, https://www.pressure-products.com/wip/tvi.html, as printed Jul. 25, 2024 in 2 pages.

Bergersen et al., "Congenital Heart Disease: The Catheterization Manual", Netherlands, Springer, 2009, pp. 115-118 and 143-150.

* cited by examiner

CONTROLLABLE INSERTION SLEEVE

BACKGROUND

Field

The present invention relates to a controllable insertion sleeve, which comprises a sleeve wall having a cavity in which a guide wire extends. The invention further relates to an insertion device comprising such an insertion sleeve.

Description of the Related Art

During surgical catheter procedures (catheter interventions) in the field of medicine, a guide wire is inserted into the (blood) vessel endovascularly via a vascular cannula or sheath, typically using the so-called Seldinger technique, and advanced to a desired end position. The guide wire is a tightly helically wound guide wire and is relatively flexible as a result of the turns. The guide wire is also equipped with a soft, flexible tip that is bent back in a semicircle to avoid perforation of the inner vessel wall along the way to the desired end position. After reaching its desired end position, the guide wire is fixed in place and the vascular cannula is removed. A hollow-cylindrical catheter can then be inserted into the (blood) vessel by threading it onto the end of the catheter away from the vessel and advanced along the guide wire. The guide wire is thereby inside the hollow-cylindrical catheter. The catheter is advanced along the guide wire until it has reached the desired end position. The guide wire is then removed from inside the catheter. The cleared interior of the hollow-cylindrical catheter can then be used to remove tissue or fluids from the interior of the (blood) vessel or introduce objects or fluids into the (blood) vessel via an opening of the hollow-cylindrical catheter.

SUMMARY

An underlying object of the invention is to further improve the devices known in the state of the art, in particular in terms of expanded insertion and placement options and a reduced risk of injury.

To achieve this object, the combination of features specified in the independent claims is proposed. Advantageous configurations and further developments of the invention emerge from the dependent claims.

A hollow-cylindrical or hose-like insertion sleeve for insertion into a vessel is proposed. The insertion sleeve comprises a cavity (wall lumen) formed in the sleeve wall and at least one control wire integrated into or mounted in the sleeve wall. The cavity extends through the insertion sleeve along its entire length parallel to its longitudinal direction or longitudinal axis. A guide wire extends inside the cavity or longitudinal channel formed in the cross-section of the sleeve wall. Using the at least one control wire, it is possible to control a curvature of the flexible insertion sleeve and thereby adapt it to the spatial course of the (blood) vessel to be negotiated in order to avoid vascular injuries when inserting the insertion sleeve.

Since the guide wire extends in a cavity formed in the sleeve wall, the interior of the hollow-cylindrical insertion sleeve is freely accessible. The insertion sleeve can be used to insert complex endovascular systems or devices, such as cameras, sensors or blood pumps, which, due to their design, do not permit a centrally positioned guide wire in the insertion sleeve, through the interior into a blood vessel.

Image recording by a camera is thereby already possible during the insertion process of the insertion sleeve.

According to one aspect of the invention, the cavity in which the guide wire extends is configured entirely within the cross-section of the sleeve wall. The outer and inner side of the sleeve wall remain unchanged in an uncurved state. In the case of the hollow-cylindrical insertion sleeve, the outer radius and the inner radius of the hollow cylinder are constant.

The sleeve wall has essentially no contour deviation in the region in which the cavity is configured in the sleeve wall of the insertion sleeve. An outer or inner contour deviation can, among other things, result in more difficult control of the curvature of the insertion sleeve when passing through the vessels, which increases the risk of injury to the surrounding vessels. An internal contour deviation also leads to a narrowing of the interior space of the insertion sleeve, which can adversely affect the entry of materials into the vessel via the interior space of the insertion sleeve.

According to a further aspect of the invention, the sleeve wall can have at least one protrusion. The cavity or profile channel in which the guide wire extends can be configured at least partially in the region of the protrusion of the sleeve wall. According to a further aspect, the cavity can be configured entirely in the protrusion of the sleeve wall. It should be noted that the protrusion(s) form a part of the sleeve wall.

The protrusions can in particular be configured to protrude outward, i.e. away from the central interior space, or inward, i.e. toward the central interior space.

The guide wire is preferably configured in accordance with the requirements of the Seldinger technique and has a soft, flexible and proximally curved tip. The guide wire designed in accordance with the requirements of the Seldinger technique is used to guide the insertion sleeve inside vessels. Using the guide wire, injuries to vessels when advancing the guide wire can be minimized and complications of the surgical procedure can be avoided.

According to one aspect, the effective length of the at least one control wire, which is integrated into or mounted in the sleeve wall, can be shortened or lengthened, as a result of which a curvature of the insertion sleeve is achieved. The at least one control wire is anchored in a non-displaceable manner at least at one location on the insertion sleeve. The pulling and/or pushing forces when the section of the control wire in the sleeve is shortened or lengthened then act on this at least one location, which enables the insertion sleeve to bend. The necessary alignment and adaptation to the respective configuration of the vessels can be carried out to ensure precise passage with as little injury to vessels or nerve tracts as possible. The insertion sleeve can thus also be placed precisely in difficult-to-access regions having a vascular curve, such as the aortic arch, for example.

The shortening or lengthening for controlling the curvature can preferably take place via isolated mechanisms or a common mechanism outside the vessel, and can be adjusted either continuously or in a fixed manner in predefined positions or steps.

A further aspect of the invention relates to a device for inserting an endovascular system, in particular a heart support system, into a blood vessel with an insertion sleeve according to the invention and a guide wire extending therein, wherein at least one control wire is disposed in the insertion sleeve in order to control a curvature of the insertion sleeve. The advantages of the insertion sleeve mentioned at the outset can thus be achieved specifically for the insertion of complex endovascular systems in difficult-to-access vascular regions without the need for a guide wire in the central cavity.

The at least one control wire is advantageously connected to the insertion sleeve in a non-displaceable manner in the region of the distal end of said insertion sleeve, so that the effective wire length can be adjusted relative to this location.

In this context, it is advantageous if the at least one control wire extends along the insertion sleeve and ends proximally in a control device. Said control device can be configured to shorten and/or lengthen the section of the at least one control wire located in the insertion sleeve.

A further improvement is achieved in that the lengths of a plurality of control wires can be adjusted relative to another in a coordinated manner.

To avoid vascular injuries, it is advantageous if an end section of the guide wire protrudes freely beyond the distal end of the insertion sleeve.

Design examples of the invention are shown schematically in the drawings and explained in more detail in the following description.

DETAILED DESCRIPTION

Figure 1:
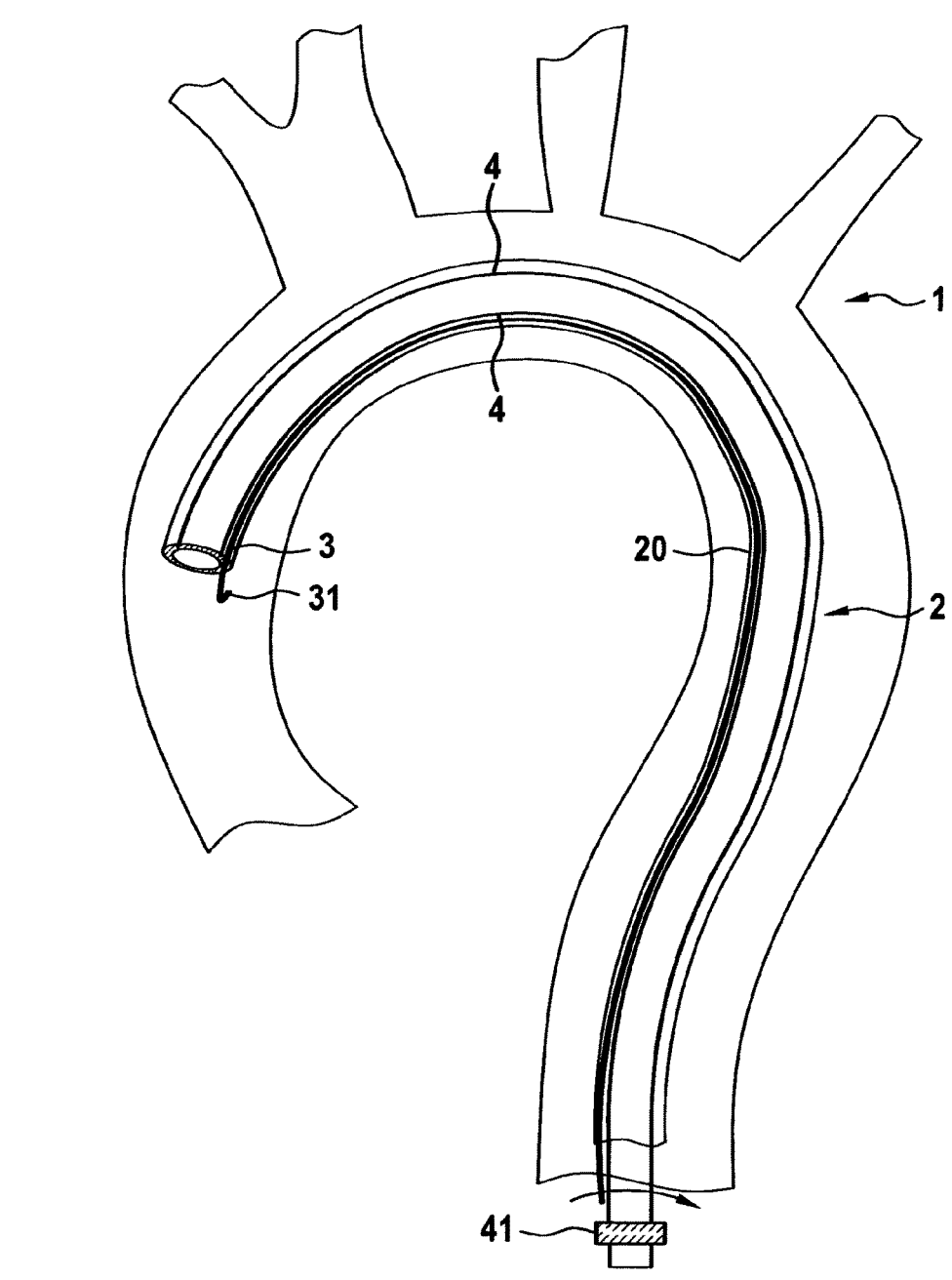
FIG. 1 shows a longitudinal section of the insertion sleeve according to the invention in a blood vessel.

FIG. 1 shows a schematic illustration of the insertion sleeve 2 according to the invention as it passes through a blood vessel 1, here the aorta. A guide wire 3 is first pushed through blood vessel 1 to a desired position. The insertion sleeve 2 is then advanced along the guide wire 3 to this position. The guide wire 3 is configured in accordance with the requirements of the Seldinger technique and has a soft, flexible tip 31 that is curved in the proximal direction. The insertion sleeve 2 follows the curvature of the guide wire 3 when it is advanced.

To bend the insertion sleeve 2, said insertion sleeve comprises control wires 4, two of which are shown in FIG. 1. The control wires 4 are connected to the insertion sleeve 2 in a non-displaceable manner at a connection point in the region of the distal end of said insertion sleeve and pass through the insertion sleeve 2 parallel to its longitudinal direction along its entire length and end in a control device 41. This control device 41 is located outside the body. The control device 41 is used to shorten or lengthen the control wires 4 up to the connection point and thus control the insertion sleeve 2 as it passes through a difficult-to-access blood vessel 1. This can take place via isolated mechanisms or a common mechanism outside the vascular system 1, for example on a twist grip or handle. The control wires can thus be shortened separately and relative to another in a coordinated manner. This ensures precise passage with as little alteration of the vessel inner wall as possible.

FIG. 2a-e show exemplary embodiments for configuring a cavity 23 in a sleeve wall 22 of the insertion sleeve 2. The hollow-cylindrical insertion sleeve 2 comprises a hollow interior space 21, which is enclosed by the sleeve wall 22. Endovascular systems or devices not shown here, such as cameras, sensors or blood pumps, for example, which are used in the blood vessel 1, are provided in this interior space 21. A cavity 23 is configured in the profile of the sleeve wall 22, inside which the guide wire 3 extends. The cavity 23 extends inside the sleeve wall 22 along the entire length of the insertion sleeve 2 parallel to the longitudinal direction or longitudinal axis of the insertion sleeve 2.

FIG. 2a-e also shows four control wires 4, which are integrated in the sleeve wall 22 and cause the curvature of the insertion sleeve 2.

Figure 2A:
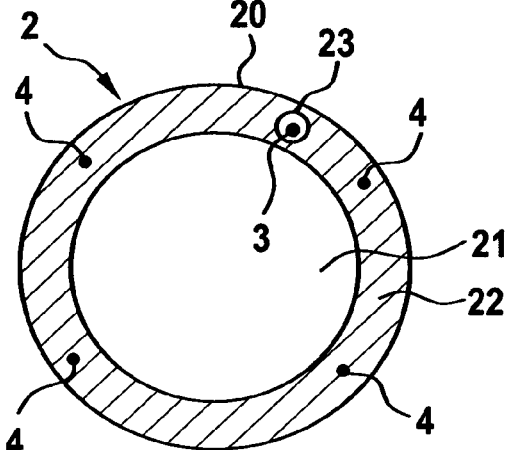
FIG. 2a-2e show, in cross-section, various ways of configuring a cavity for receiving a guide wire in the sleeve wall of the insertion sleeve.

FIG. 2a-e show a variety of options for configuring the cavity 23 with the guide wire 3 extending therein in the sleeve wall 22. In FIG. 2a, the cavity 23 is configured entirely within the sleeve wall 22 without reshaping or changing the outer and inner contour of the sleeve wall 22 in the region of the cavity 23.

Figure 2B:
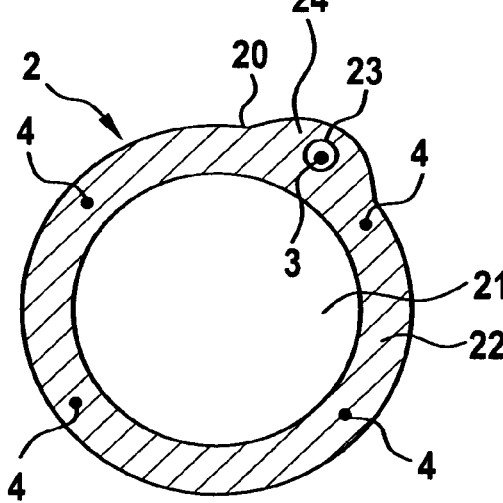

In FIG. 2b, the cavity 23 is configured partially in a bulge or protrusion 24 on the outer side of the sleeve wall 22.

Figure 2C:
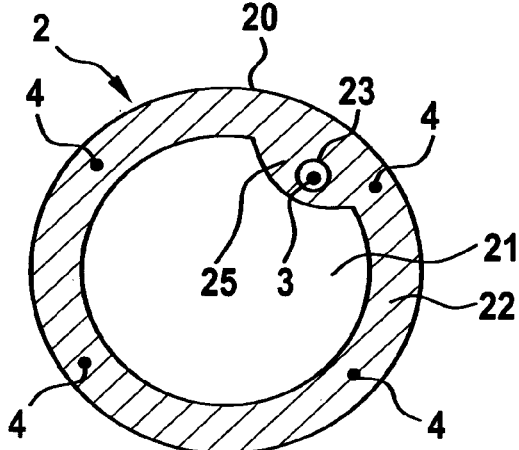

In FIG. 2c, the cavity 23 is configured partially in a protrusion 25 on the inner side of the sleeve wall 22.

Figure 2D:
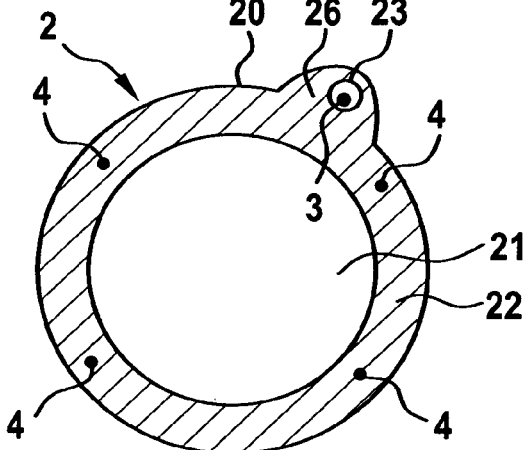

In FIG. 2d, the cavity 23 is configured entirely in a protrusion 26 on the outer side of the sleeve wall 22.

Figure 2E:
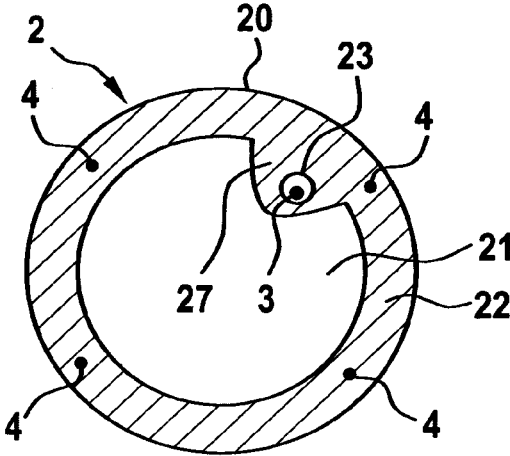

In FIG. 2e, the cavity 23 is configured entirely in a protrusion 27 on the inner side of the sleeve wall 22.

The invention claimed is:

1. An endovascular insertion sleeve configured to receive a guide wire for guiding the insertion sleeve, the insertion sleeve comprising:
   a central cavity formed in the insertion sleeve, the central cavity having a center that is coaxial with a center of the insertion sleeve, the central cavity having a circular cross-sectional profile; and
   a second cavity formed in a wall of the insertion sleeve, wherein the second cavity extends parallel to a longitudinal direction of the insertion sleeve over an entire length of the insertion sleeve, wherein the second cavity is configured to receive the guide wire extending in the second cavity, wherein at least one control wire is integrated within the insertion sleeve, wherein the at least one control wire is configured to control a curvature of the insertion sleeve, and wherein the second cavity is positioned radially outward from the circular cross-sectional profile of the central cavity of the insertion sleeve throughout the entire length of the insertion sleeve.

2. The insertion sleeve according to claim 1, wherein the second cavity is positioned entirely within the sleeve wall.

3. The insertion sleeve according to claim 1, wherein the guide wire has a soft, flexible and proximally curved tip.

4. The insertion sleeve according to claim 1, wherein the at least one control wire is configured to be shortened and/or lengthened to control the curvature of the insertion sleeve.

5. The insertion sleeve according to claim 1, wherein an effective length of the at least one control wire is continuously adjustable or adjustable in predefined steps.

6. A device for inserting an endovascular system into a blood vessel, comprising:
   an insertion sleeve comprising:
      a central cavity formed in the insertion sleeve, the central cavity having a center that is coaxial with a center of the insertion sleeve, the central cavity having a circular cross-sectional profile; and
      a second cavity formed in a wall of the insertion sleeve, wherein the second cavity extends parallel to a longitudinal direction of the insertion sleeve over an entire length of the insertion sleeve, and wherein the second cavity is positioned radially outward from the circular cross-sectional profile of the central cavity of the insertion sleeve throughout the entire length of the insertion sleeve; and a guide wire configured to extend within the second cavity of the insertion sleeve, wherein at least one control wire is disposed in the insertion sleeve, and wherein the at least one control wire is configured to control a curvature of the insertion sleeve.

7. The device according to claim 6, wherein the at least one control wire is connected to the insertion sleeve in a non-displaceable manner in a region of a distal end of the insertion sleeve.

8. The device according to claim 6, wherein the at least one control wire extends along the insertion sleeve and ends proximally in a control device.

9. The device according to claim 8, wherein the control device is configured to shorten and/or lengthen a section of the at least one control wire located in the insertion sleeve.

10. The device according to claim 6, wherein the at least one control wire comprises a plurality of control wires comprising lengths configured to be adjustable relative to one another in a coordinated manner.

11. The device according to claim 6, wherein an end section of the guide wire protrudes freely beyond a distal end of the insertion sleeve.

<center>* * * * *</center>